United States Patent [19]

Kaster et al.

[11] 4,211,241
[45] Jul. 8, 1980

[54] HEART VALVE SIZING GAUGE

[75] Inventors: Robert L. Kaster, Wayzata; Donald N. Mehl, Minnetonka, both of Minn.

[73] Assignee: Kastec Corporation, Plymouth, Minn.

[21] Appl. No.: 882,971

[22] Filed: Mar. 3, 1978

[51] Int. Cl.² ........................... A61B 5/10; G01B 5/12
[52] U.S. Cl. ................................. 128/774; 33/174 D; 33/178 B; 128/303 R
[58] Field of Search .................. 128/2 S, 303 R, 343, 128/345, 305, 774; 33/174 D, 178 B, 168 R

[56] References Cited

U.S. PATENT DOCUMENTS

| | | | |
|---|---|---|---|
| 1,934,513 | 11/1933 | Schulte | 128/324 |
| 2,376,893 | 5/1945 | Baker | 128/305 |
| 2,473,968 | 6/1949 | Paton | 128/305 |
| 2,617,201 | 11/1952 | Davies | 33/178 B |
| 3,177,874 | 4/1965 | Spriggs | 128/303 R |

OTHER PUBLICATIONS

"The Lilleheikaster Pivoting Disc Prosthetic Heart Valve," put out by Medical, Inc., pages bearing Rev 11/72.
Page from Pub. of Edwards Labs., Div. of Amer. Hospital Supply Corp., bearing Litho in USA 104461, 1/72, Rev 5/73 11P 1—1—3.

Primary Examiner—Robert W. Michell
Assistant Examiner—Michael H. Thaler
Attorney, Agent, or Firm—Hugh D. Jaeger; Joseph F. Breimayer; Lew Schwartz

[57] ABSTRACT

A sizing gauge for determining the proper size of heart valve for implantation in a natural heart valve orifice. The sizing gauge includes a handle which can be gripped by a surgeon, a sizing ring having a smooth outer surface and a hollow interior, and connecting struts connecting the sizing ring and the handle. The connecting struts is so constructed and arranged as to afford direct visual observation by the surgeon of heart tissue beyond the sizing ring when the latter is inserted in a heart orifice. Outer surfaces of the connecting struts diverge forwardly for connection to the sizing ring and merge with the outer surface of the sizing ring to permit the latter to be eased outwardly through the natural heart valve orifice.

14 Claims, 9 Drawing Figures

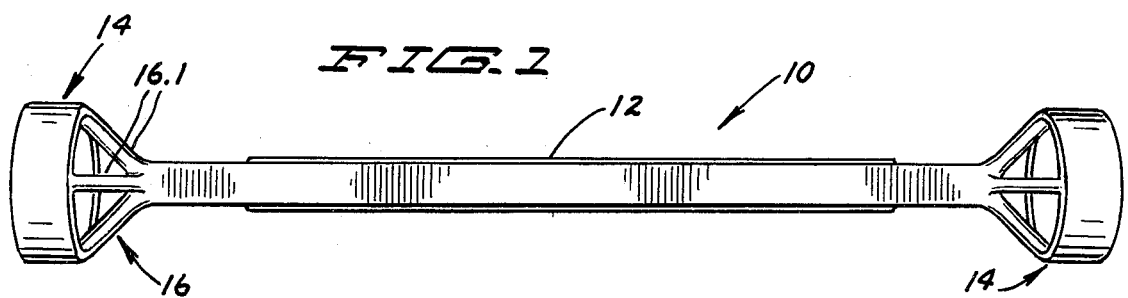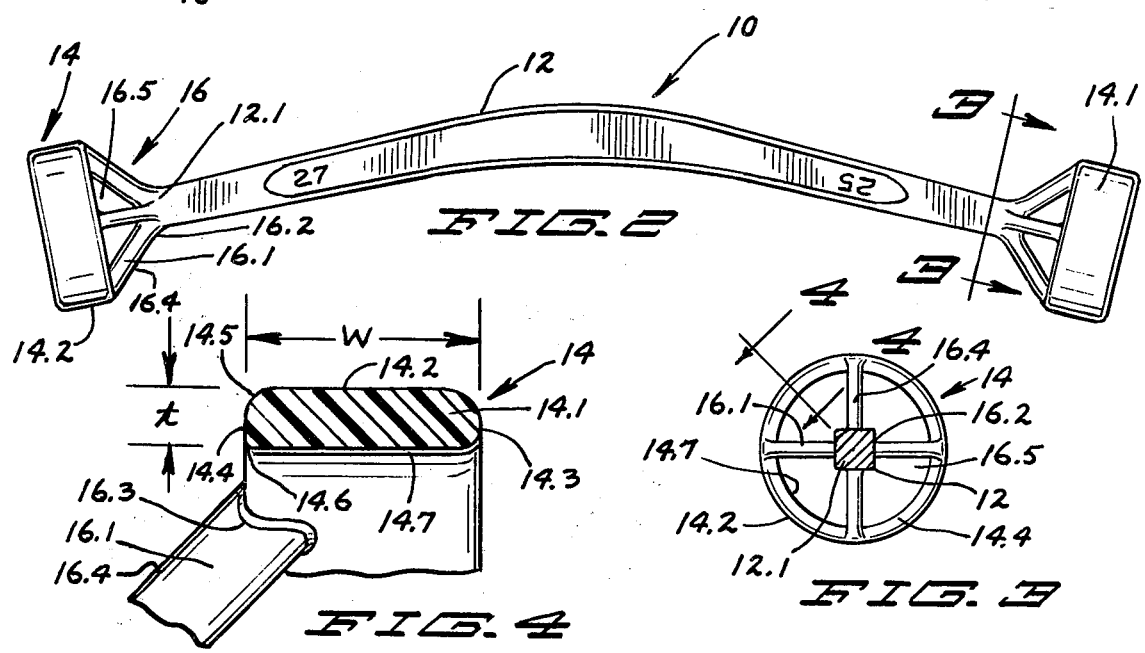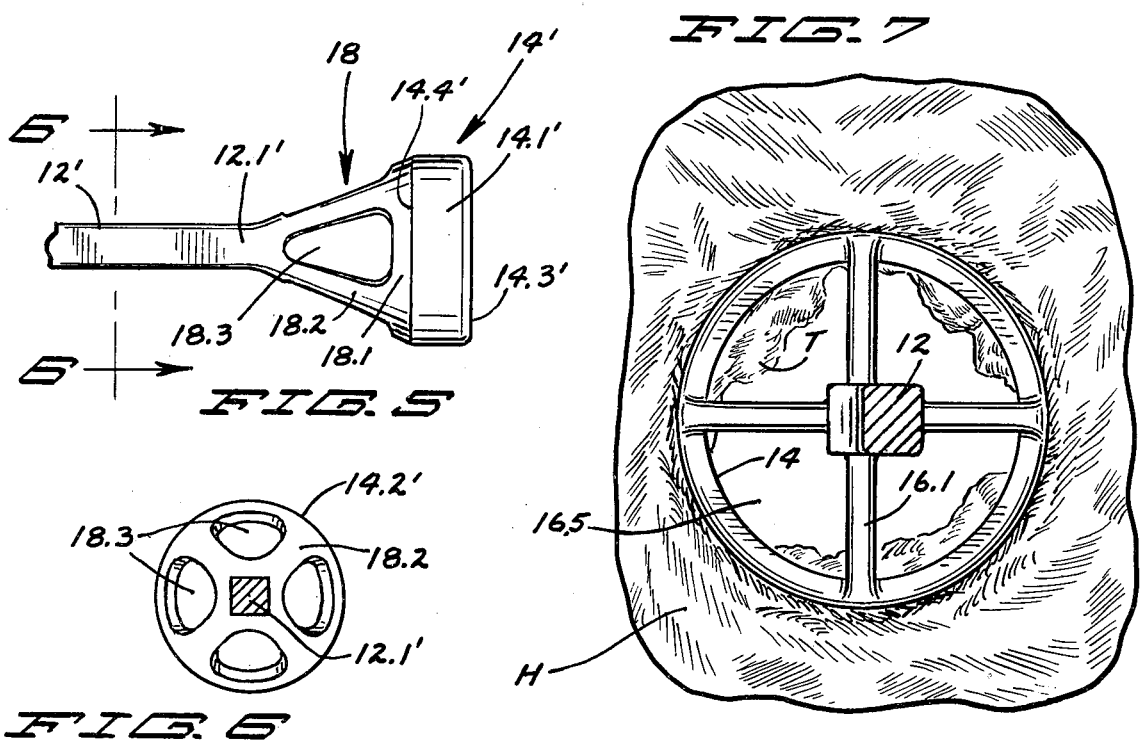

HEART VALVE SIZING GAUGE

BACKGROUND OF THE INVENTION

Damaged heart valves are now often replaced with mechanical valves of the type described, for example, in U.S. Pat. No. 4,021,863. Mechanical valves are commonly provided with a generally circular base about which is provided a suturing ring. In the process of implanting a mechanical heart valve, the natural valve orifice is prepared by surgical removal of damaged or diseased valve tissue, leaving the orifice with an open, generally circular configuration. The mechanical valve of proper size is then appropriately affixed in the natural valve orifice by stitching the suturing ring to the surrounding valve orifice tissue. The sizes of natural heart valve orifices may vary considerably between patients, and the sizes of the valve orifices for the different valves of the heart may vary as well. For example, there are significant size differences even in a normal heart between mitral, aortic, tricuspid and pulmonary valve orifices. To avoid undue stresses on sutured heart valve orifices, and to provide optimum implant results, good practice suggests that the surgeon measure the orifice size with a measuring gauge, and then select an appropriately sized mechanical valve.

Measuring gauges of the type referred to above have been provided in a series of sizes, the gauges having cylindrical end portions of given diameters. The sizing operation involves selecting that particular gauge that exhibits the desired "fit" in a natural heart valve orifice. One such gauge comprises a handle having at its forward end a cup-shaped device, the flat, closed bottom of the cup facing forwardly away from the handle. This gauge, in modified form, includes a flange extending radially outwardly from the rearward open mouth of the cup-shaped device. Yet another gauge is provided with a finger-like projection having a smooth, bullet-shaped nose at its forward end and an outwardly diverging skirt at its rearward end, the projection being attached to a rearwardly extending handle.

Although positive results have been obtained using such gauges (often termed "obturators"), certain problems have arisen with the use of such devices. The gauges of the type described above interfere with and largely block the surgeon's view of the interior of heart chambers during the sizing operation, since such devices, even though made of transparent material, rapidly become obscured by blood. It should also be observed that additional surgical removal of annular heart tissue within or adjacent to an orifice is often necessary to permit the mechanical valve to be properly accomodated and to remain operable within the natural heart valve orifice. The sizing gauges referred to above, however, tend to indicate orifice size only, and do not permit the surgeon to view the inwardly visible external periphery of the natural heart valve orifice. Further, there is a risk that certain of the gauges, such as those employing the cup-shaped elements referred to above, may actually pass through an orifice to be sized and into a heart chamber on the other side of the orifice. The relatively sharp edges at the rearward portion of gauges of this type render their removal back through the valve orifice not only difficult to accomplish, but potentially traumatic to the annular heart tissue.

Insertion of such (prior art) sizing gauges within a heart orifice such as the aortic valve orifice may produce pressurization of the heart cavity beyond the valve. For example, when the sizing procedure is employed for the aortic valve from the aortic aspect, the left ventricle may become pressurized, the sizing gauge sliding through the valve orifice in much the same manner that a piston slides through a cylinder. When the surgeon encounters resistance to further insertion of the sizing gauge due to cavity pressurization, the resistance may erroneously be interpreted to a supposed contact of the sizing gauge with annular heart tissue and may result in inaccurate gauging of the tissue orifice and a consequent poor choice of mechanical valve size.

There is thus a clear need in the surgical field for a valve sizing gauge which would not obstruct the surgeon's view during the sizing operation. It is also desirable to provide a sizing gauge which, following inadvertent passage of the gauge through a heart orifice, could be easily retrieved through the orifice with a minimum of difficulty and trauma.

SUMMARY OF THE INVENTION

The present invention provides a heart valve gauge affording direct visual observation of peripheral heart valve tissue during the sizing operation. In its preferred embodiment, the gauge may be easily withdrawn from a heart orifice with minimum trauma to the heart tissue. The gauge comprises a handle and a sizing ring which has a smooth continuous exterior wall and an open, hollow interior. Connector means are provided to connect the handle to the sizing ring. The connector means are so constructed and arranged as to permit direct visual observation through the interior of the sizing ring of heart tissue beyond the ring, and provides an air passage outwardly from the interior of the ring. The connector may take the form of a hollow, generally conical section attached near its vertex rearwardly to the handle and attached at its forward, open end to the sizing ring, the connector having openings which are so positioned as to afford direct visual observation through the openings and through the interior of the sizing ring. In another embodiment, the connector may include a plurality of struts, each connected at one end rearwardly to the handle and thence diverging from one another for connection forwardly to the periphery of the sizing ring. The struts define between them openings permitting visual observation through the interior of the sizing ring. In general, the exterior surface of the connector means is desirably smooth, and, as mentioned, diverges outwardly for connection to the sizing ring, the exterior surface of the sizing ring and connector means thereby providing a smooth surface facilitating removal of the sizing ring from a heart orifice.

DESCRIPTION OF THE DRAWING

FIG. 1 is a top view of a sizing gauge of the invention;

FIG. 2 is a side view of the sizing gauge of FIG. 1;

FIG. 3 is a cross-sectional view taken along line 3—3 of FIG. 2;

FIG. 4 is a broken-away, cross-sectional view taken along line 4—4 of FIG. 3;

FIG. 5 is a broken-away view of another embodiment of the sizing gauge of the invention;

FIG. 6 is a cross-sectional view taken along line 6—6 of FIG. 5;

FIG. 7 is a broken-away view in partial cross-section, showing the sizing gauge of FIG. 1 inserted into a heart orifice;

DETAILED DESCRIPTION

Figure 8:
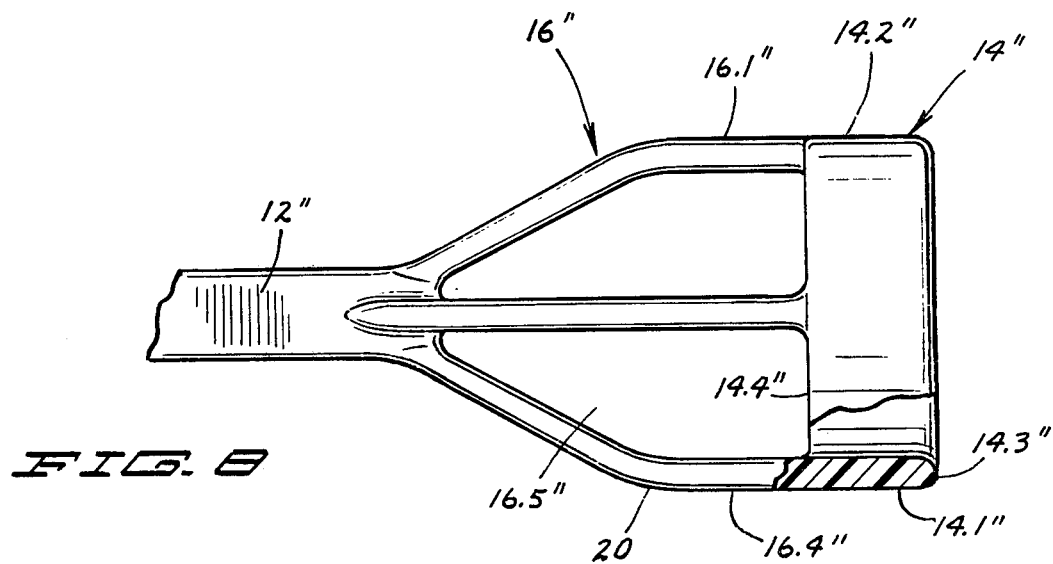
FIG. 8 is a broken-away view in partial, cross-section of another embodiment of the invention.

Referring first to FIGS. 1-4 and 7, the gauge of the invention is designated generally as 10 and includes a handle 12 at either end of which is positioned a sizing ring 14. The handle has a slight bend intermediate its ends to facilitate use of the gauge in the physically confining environment encountered in heart surgery. The handle may have a sizing ring at each end, as shown in the drawing, or may be provided with a sizing ring on but a single end. As shown in FIG. 2, numbers may be provided on the handle adjacent its ends to indicate the diameter of the respective sizing ring or the size of the corresponding mechanical heart valve. The numbers in FIG. 2 designate valve sizes of 25 mm. and 27 mm., respectively.

For ease of description, the invention will be described with respect to sizing gauges having sizing rings on but a single end, it being understood that the preferred embodiment of the invention employs a sizing ring on both ends of the handle.

The handle and sizing ring are rigidly connected by connector means designated generally as 16 in FIGS. 1 and 2 and as 18 in FIG. 5.

The sizing ring comprises an annular ring of plastic or other material, and has open ends. The thickness of the wall 14.1 (indicated as "t" in FIG. 4) of the ring is quite small in comparison with its overall diameter and may be on the order of 2.25 mm. The width of the ring, measured parallel to its axis and indicated as "w" in FIG. 4, is desirably reasonably large and may be on the order of $\frac{1}{4}$ to $\frac{1}{2}$ of the outer diameter of the ring. The outer surface 14.2 of the ring is desirably smooth and unbroken, and is generally parallel to the axis of the ring. The leading edge 14.3 (FIG. 4) of the ring is smoothly curved to permit the ring to be eased into a natural tissue orifice and to avoid tissue damage, and the trailing end 14.4 of the ring is similarly rounded at its outer periphery 14.5 and may be sharply edged or rounded at its inner periphery 14.6. Inner surface 14.7 of the ring is also desirably smooth and generally parallel with the ring's axis. The thickness "t" of the wall of the ring is thus sufficiently great to provide a gently rounded leading edge 14.3, and is yet sufficiently small as to minimally, if at all, interfere with the field of view through the open interior of the ring.

FIGS. 1-4 and 7 depict the connector means as a plurality of struts 16.1, each strut being attached at one end, termed the rearward end 16.2, to the adjacent end 12.1 of the handle. The struts diverge forwardly, as shown best in FIGS. 1 and 2, and are attached at their forward ends 16.3 to the trailing edge of the sizing ring, the outer surfaces 16.4 of the struts merging into the outer surface 14.2 of the sizing ring. For strength, the forward end 16.3 of the struts may wrap inwardly slightly of the trailing edge of the sizing ring, as shown best in FIG. 4. For reasons of cleanliness and to avoid high stress concentrations, internal corners at the points of attachment of the handle and ring to the connector means are gently rounded.

The confronting surfaces of adjacent struts define between them rather large openings 16.5, the openings being generally wedge-shaped and extending a significant distance radially inwardly of and rearwardly from the sizing ring toward the adjacent end of the handle. In this manner, the spaces 16.5 between the struts provide the surgeon with an excellent field of view through the interior of the sizing ring. Desirably, the openings 16.5 are four in number and are arranged equiangularly about the circumference of the connector.

FIG. 7 depicts the gauge of FIGS. 1-4 in position within a valve orifice of a heart H, and is representative of the surgeon's view during the valve sizing operation. In FIG. 7, folds of tissue T just beyond the leading edge of the ring are seen to protrude inwardly beyond the leading edge of the ring and into the surgeon's view, thus providing the surgeon with the opportunity of excising such tissue to prevent later interference with the action of the heart valve to be implanted.

The embodiment shown in FIGS. 5 and 6 is similar to that shown in FIGS. 1-4 and 7, and primed numbers have been employed to designate elements of the gauge of FIGS. 5 and 6 which correspond to the same or similar elements of the gauge of FIGS. 1-4 and 7. The embodiment of FIGS. 5 and 6 employs a generally cone-shaped, hollow connector 18 which is coaxial with the sizing ring 14'. The forward, open end 18.1 of the connector is attached about its periphery to the trailing edge 14.4' of the sizing ring, and has an exterior surface 18.2 which is blended into the exterior surface 14.2' of the sizing ring. The outer wall of the connector converges rearwardly for connection to the end 12.1' of a handle 12'. Again, internal corners are gently rounded for purposes of strength and cleanliness. A series of openings 18.3 are provided as viewing ports about the circumference of the connector to permit a surgeon to view internal orifice tissue in substantially the same manner as described above with respect to the embodiment of FIGS. 1-4 and 7. The smooth, generally slippery outer walls 18.2 of the connector may be employed to aid in gentle removal of the sizing ring from a heart orifice by exerting gentle outward pressure on the orifice as the sizing ring is withdrawn, all in a manner similar to that of the previously described embodiment. The openings 18.3 are preferably as large as possible consonant with providing the gauge with rigidity and strength.

FIG. 8 depicts further embodiment of the invention, and double primed numbers have been employed to designated elements of this gauge that correspond to the same or similar elements of the gauge of FIGS. 1-4 and 7. The embodiment depicted is similar to that of FIGS. 1-4 and 7 except that the struts 16.1" extend axially rearwardly from the sizing ring 14", and then undergo to a gentle bend (at 20) and converge rearwardly for attachment to the handle 12". The openings 16.5" between the struts are somewhat larger than are the openings 16.5 of the gauge depicted in FIGS. 1-4 and 7, thereby further increasing the ease of visual observation of heart valve tissue by a surgeon. The thickness of the struts 16.1", measured radially with respect to the axis of the sizing ring, may be the same as the thickness of the wall 14.1" of the sizing ring, or may be thicker or thinner than the sizing ring wall. The outer surfaces 16.4" of the struts smoothly merge into the outer surface 14.2" of the sizing ring. As previously described, sharp edges and corners are avoided for purposes of strength and cleanliness.

Figure 9:
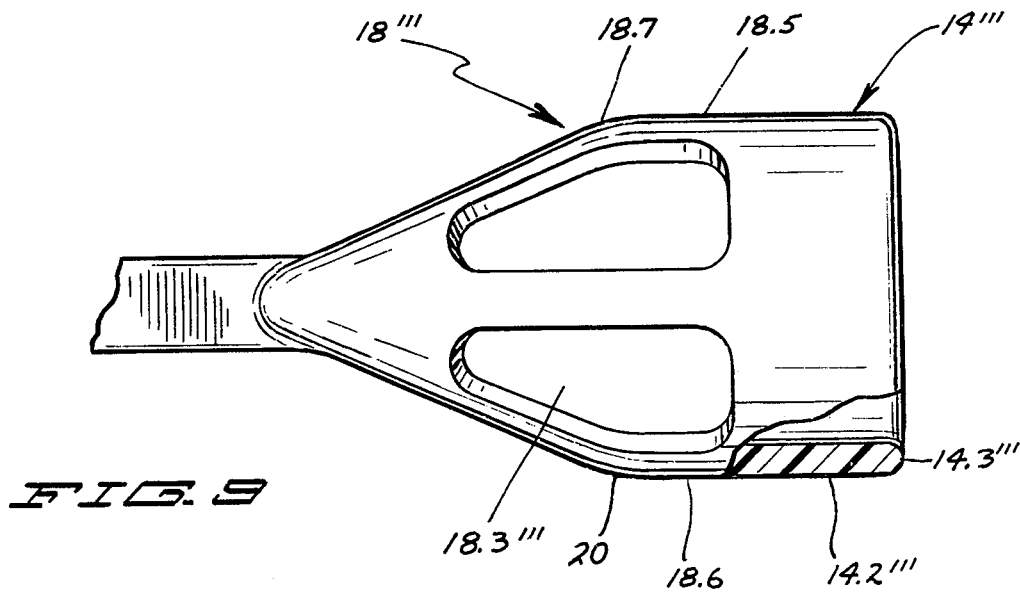
FIG. 9 is a broken-away view in partial, cross-section of yet another embodiment of the invention.

FIG. 9 depicts another embodiment of the invention, and triple primed numbers have been employed to designate elements of this gauge that correspond to the same or similar elements of the gauges of FIGS. 1-7.

The gauge of FIG. 9 employs a generally cone-shaped, hollow connector 18''' which has a cylindrical portion 18.5 at its forward end, the cylindrical portion having exterior walls 18.6 which merge into the exterior walls 14.2''' of the sizing ring. The juncture 18.7 of the conical and cylindrical portions of the connector is smoothly rounded, as depicted. A series of openings 18.3''' are provided through the walls of the connector about its circumference in a manner similar to the embodiment shown in FIGS. 5 and 6, the openings permitting the surgeon a good field of view in substantially the same manner as described above in connection with the embodiment of FIG. 8. The openings 18.3''' may be somewhat larger than the openings 18.3 in the embodiment of FIGS. 5 and 6 to improve the field of view. The openings 18.3''' are preferably four in number, and desirably are formed not only in the conical portion of the connector, but extend into the cylindrical portion thereof as well.

Although the gauge of the invention has thus far been described as having four viewing openings or ports in the connector, it will be evident that the number of ports which are employed may be a greater or lesser number. For example, the gauges of FIGS. 1 and 8 may be provided with connector means having but a single strut 16.1, 16.1" extending from the handle to the sizing ring, thereby providing a single, large viewing port. When more than one viewing port is employed, it is desirable but not critical that the ports be spaced equally about the circumference of the connector. Preferred embodiments of the invention employ four ports, as mentioned, but the number of ports may vary from one to six or more as desired.

The sizing ring of the invention may be made of a medically acceptable material such as various polymeric materials, stainless steel, titanium and the like. Preferably, the gauge is made of a high strength, temperature resistant polymeric material such as medical grade polysulfone, a thermoplastic material produced by Union Carbide Corporation under the trade name "Udel". At least nominal temperature stability is desired so that the gauge of the invention may reasonably withstand the rigors of autoclave on ethylene oxide sterilization without degradation or warping. Other suitable polymers include polytetrafluroroethylene, polycarbonate and polypropylene. The gauge is desirably molded in one piece by known injection molding techniques to facilitate manufacture, to reduce cost, to provide surface smoothness and to avoid glue lines, weldments, interference fits and the like which might weaken the gauge.

Various other adaptations of the described embodiments will now be apparent to the skilled artisan, and are within the scope of the instant invention. For example, the trailing edge 14.4 of the sizing ring may be provided with a flange or lip extending generally radially outwardly to restrain the sizing ring from inadvertently passing completely through a natural heart orifice. Moreover, the handle or connector means or both may be provided with a bent configuration as desired to facilitate maneuvering of the gauge during the sizing operation.

Thus, a heart valve sizing gauge has been provided that permits a surgeon to directly view heart tissue beyond the sizing ring of the gauge and that prevents pressurization of a heart cavity during the sizing operation by providing an open passage for fluid pressure relief. Moreover, the sizing ring is easily withdrawn from a heart orifice, and produces minimal trauma during a sizing operation.

It will be understood that the use herein of "heart valve", heart "chamber" and the like refers to valves and chambers in veins and arteries leading to and from the heart as well as those valves between heart chambers, and includes aortic pulmonary, mitral and tricuspid valves. "Direct" visual observation means observation unhindered by transparent panels, walls or the like.

While a preferred embodiment of the invention has been described, it should be understood that various changes, adaptations, and modifications may be made therein without departing from the spirit of the invention and the scope of the appended claims.

What is claimed is:

1. A heart valve sizing gauge comprising a slightly curved handle, a right circular cylindrical sizing ring having a smooth continuous exterior wall of a width, as measured parallel to the ring axis, substantially greater than the wall thickness and a hollow interior, and connector means connecting the handle and the sizing ring, wherein the connector means is connected rearwardly to the handle and includes exterior surface means diverging forwardly and smoothly, unbrokenly blending into the exterior surface of the sizing ring to facilitate removal of the sizing gauge ring from the heart orifice, and so constructed and arranged for providing direct visual observation through the interior of the sizing ring of heart tissue beyond the sizing ring.

2. The heart valve sizing gauge of claim 1 wherein the connecting means comprises a connector provided with openings therein so arranged as to permit direct visual observation therethrough and through the sizing ring of heart tissue beyond the ring.

3. The heart valve sizing gauge of claim 1 in which the connector means comprises a plurality of spaced struts defining between them said openings.

4. The heart valve sizing gauge of claim 3 wherein at least a portion of the struts are forwardly divergent, the struts having outer surfaces merging forwardly into the outer surface of the sizing ring, the struts being connected rearwardly to the handle.

5. The heart valve sizing gauge of claim 1 wherein the exterior wall of the sizing ring is free of exterior projections retarding insertion of the ring into a heart orifice.

6. The heart valve sizing gauge of claim 1 wherein the connector means includes openings therethrough so positioned as to permit direct visual observation through the openings and through the interior of the sizing ring of heart tissue beyond the sizing ring.

7. A heart valve sizing gauge permitting direct visual observation of interior heart valve tissue, the gauge comprising a slightly curved handle, a right circular cylindrical sizing ring having a smooth continuous exterior wall of a width, as measured parallel to the ring axis, substantially greater than the wall thickness and a generally unobstructed, open interior, and connector means comprising a plurality of spaced struts, each strut being connected at its rearward end to the handle and the struts diverging forwardly and smoothly connected at their forward ends to the sizing ring, the struts having smooth exterior surfaces merging at their forward ends with the exterior surface of the sizing ring, the spaced struts defining between them openings permitting direct visual observation therethrough and through the interior of the sizing ring of heart tissue beyond the sizing ring.

8. The sizing gauge of claim 7 wherein the struts are arranged equiangularly about the periphery of the sizing ring.

9. The sizing gauge of claim 8 wherein said struts are four in number.

10. A heart valve sizing gauge permitting direct visual observation of interior heart tissue, the gauge comprising a slightly curved handle, a right circular cylindrical sizing ring having a smooth continuous exterior wall of a width, as measured parallel to the ring axis, substantially greater than the wall thickness and a generally unobstructed open interior, and connector means comprising a hollow, generally cone-shaped connector positioned generally coaxially of the sizing ring, the connector having a forward, open end connected about its periphery to the periphery of the sizing ring and a rearward end connected to the handle, the connector having an exterior, forwardly divergent surface smoothly merging with the exterior wall of the sizing ring and having a plurality of openings therein so oriented as to permit direct visual observation therethrough and through the interior of the sizing ring of heart tissue beyond the sizing ring.

11. The sizing gauge of claim 10 in which the openings are equally spaced about the circumference of the connector.

12. A heart valve sizing gauge permitting direct visual observation of interior heart tissue, the gauge comprising a slightly curved handle, a right circular cylindrical sizing ring having a smooth exterior wall of a width, as measured parallel to the ring axis, substantially greater than the wall thickness and a hollow interior, and connector means comprising a plurality of spaced struts, each strut having a forward portion extending generally parallel to the access of the sizing ring and joined to the latter at its forward end, and a rearward portion converging rearwardly for connection to the handle, the struts having smooth, exterior surfaces smoothly merging at their forward ends with the exterior surface of the sizing ring and the struts defining between them openings permitting a direct visual observation therethrough and through the interior of the sizing ring of heart tissue beyond the sizing ring.

13. A heart valve sizing gauge permitting direct visual observation of interior heart tissue, the gauge comprising a slightly curved handle, a right circular cylindrical sizing ring having a smooth exterior wall of a width, as measured parallel to the ring axis, substantially greater than the wall thickness and a hollow interior, and connector means comprising a hollow connector, the connector having a generally cylindrical forward portion connected at its forward end to the sizing ring, and a generally conical rearward portion connected at its rearward end to the handle, the connector having an exterior surface smoothly, unbrokenly merging with the exterior wall of the sizing ring and having a plurality of openings therein so oriented so as to permit direct visual observation therethrough and through the interior of the sizing ring of heart tissue beyond the sizing ring.

14. A heart valve sizing gauge comprising a slightly curved handle, a pair of right circular cylindrical sizing rings of different diameters and each having a smooth, continuous exterior wall of a width, as measured parallel to the ring axis, substantially greater than the wall thickness and a hollow interior, and connector means connecting each sizing ring to a respective end of the handle wherein each connector means comprises a plurality of spaced struts, each strut being connected at one end to the handle and the struts diverging toward the sizing ring for connection at their other ends to the sizing ring, the struts having smooth exterior surfaces smoothly, unbrokenly merging at their forward ends with the exterior surface of the sizing ring and the struts defining between them openings providing direct visual observation therethrough and through the interior of the sizing ring.

* * * * *